United States Patent
Kramer et al.

(10) Patent No.: US 10,827,924 B2
(45) Date of Patent: Nov. 10, 2020

(54) DYNAMIC ILLUMINATION DURING RETINAL BURST IMAGING

(71) Applicant: Verily Life Sciences LLC, Mountain View, CA (US)

(72) Inventors: Ryan Kramer, San Francisco, CA (US); Sam Kavusi, Menlo Park, CA (US); Eliezer Glik, San Francisco, CA (US); Honglei Wu, South San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 225 days.

(21) Appl. No.: 16/031,380

(22) Filed: Jul. 10, 2018

(65) Prior Publication Data

US 2019/0046031 A1 Feb. 14, 2019

Related U.S. Application Data

(60) Provisional application No. 62/545,234, filed on Aug. 14, 2017.

(51) Int. Cl.
| | | |
|---|---|---|
| *A61B 3/12* | (2006.01) | |
| *A61B 3/14* | (2006.01) | |
| *A61B 3/00* | (2006.01) | |

(52) U.S. Cl.
CPC .............. *A61B 3/14* (2013.01); *A61B 3/0008* (2013.01); *A61B 3/12* (2013.01); *A61B 3/005* (2013.01)

(58) Field of Classification Search
CPC .. A61B 3/14; A61B 3/102; A61B 3/12; A61B 3/0008; A61B 3/13; A61B 5/0066; A61B 3/10; A61B 3/0058
USPC ................................ 351/221, 246, 206, 205
See application file for complete search history.

(56) References Cited

U.S. PATENT DOCUMENTS

| | | |
|---|---|---|
| 4,834,528 A | 5/1989 | Howland et al. |
| 6,733,129 B2 | 5/2004 | Masaki |
| 7,458,685 B2 | 12/2008 | Liang et al. |
| 7,499,634 B2 | 3/2009 | Yogesan et al. |

(Continued)

FOREIGN PATENT DOCUMENTS

| | | |
|---|---|---|
| JP | 2017-099717 A | 6/2017 |
| WO | 2012018991 A1 | 8/2010 |

OTHER PUBLICATIONS

International Search Report and Written Opinion from the International Searching Authority dated Oct. 18 2018, for International Application No. PCT/US2018/044849, filed Aug. 1, 2018, 8 pages.
E. DeHoog et al., "Optimal Parameters for Retinal Illumination and Imaging in Fundus Cameras", Optical Society of America, vol. 47, No. 36, Dec. 20, 2008, 9 pages.
de Matos, L. et al., "Coaxial Fundus Camera for Ophthalmology", Proc. of SPIE vol. 9578, Jun. 23, 2016, 5 pages.

(Continued)

*Primary Examiner* — Hung X Dang
(74) *Attorney, Agent, or Firm* — Christensen O'Connor Johnson Kindness PLLC

(57) ABSTRACT

A technique for retinal images includes configuring a dynamic illuminator to illuminate the retina with an illumination pattern. An image frame of the retina is captured while illuminated with the illumination pattern. The configuring and the capturing are iterated to sequentially reconfigure the dynamic illuminator to illuminate the retina with a plurality of different illumination patterns and to capture a plurality of image frames each illuminated with one of the different illumination patterns. The image frames are combined into a composite retinal image.

27 Claims, 8 Drawing Sheets

(56) References Cited

U.S. PATENT DOCUMENTS

| | | | |
|---|---|---|---|
| 7,878,653 B2 | 2/2011 | Ichikawa et al. | |
| 7,954,949 B2 | 6/2011 | Suzuki | |
| 8,408,464 B2 | 4/2013 | Zhu et al. | |
| 8,684,529 B2 | 4/2014 | Johansson et al. | |
| 8,811,657 B2 | 8/2014 | Teiwes et al. | |
| 8,896,842 B2 * | 11/2014 | Bower | A61B 3/102 356/497 |
| 8,955,971 B2 | 2/2015 | Ichikawa et al. | |
| 9,125,559 B2 | 9/2015 | Kersting et al. | |
| 9,271,646 B2 | 3/2016 | Neal et al. | |
| 9,289,122 B2 | 3/2016 | Chinnock et al. | |
| 2004/0085542 A1 | 5/2004 | Soliz et al. | |
| 2013/0010259 A1 | 1/2013 | Carnevale | |
| 2013/0057828 A1 | 3/2013 | de Smet | |
| 2013/0194548 A1 | 8/2013 | Francis et al. | |
| 2013/0208243 A1 | 8/2013 | Sakagawa | |
| 2013/0329189 A1 | 12/2013 | Mizucchi | |
| 2014/0085603 A1 | 3/2014 | Su et al. | |
| 2014/0240666 A1 | 8/2014 | Ootsuki | |
| 2016/0029877 A1 | 2/2016 | Murphy | |
| 2016/0174838 A1 | 6/2016 | Herranen et al. | |
| 2016/0302665 A1 | 10/2016 | Swedish et al. | |
| 2016/0317031 A1 | 11/2016 | Yang et al. | |
| 2016/0338589 A1 | 11/2016 | Carrasco-Zevallos et al. | |
| 2017/0367574 A1 | 12/2017 | Belthangady et al. | |

OTHER PUBLICATIONS

TRC-NW8 Non-Mydriatic Retinal Camera, Topcon Medical Systems, Inc., downloaded from internet on Aug. 31, 2016, 1 page.
Construction of an Inexpensive, Hand-Held Fundus Camera through Modification of a Consumer "Point-and-Shoot camera", Invest Ophthalmol. Vis Sci vol. 53, No. 12, Nov. 9, 2012, 10 pages.
Centrevue Company Profile, http://www.centervue.com, downloaded from Internet on Aug. 31, 2016, 5 pages.
EyeSelfie: Self Directed Eye Alignment using Reciprocal Eye Box Imaging, http://web.media.mit.edu/~tswedish/projects/eyeSelfie. html, downloaded form internet on Aug. 31, 2016, 3 pages.
Sugita, M. et al., "Motion Artifact and Speckle Noise Reduction in Polarization Sensitive Optical Coherence Tomography by Retinal Tracking", Biomedical Optics Express vol. 5, No. 1, Jan. 1, 2014, 17 pages.
Bengtsson, B. et al., "A New Generation of Algorithms for Computerized Threshold Perimetry, SITA", Acta Ophthalmol. Scand., 1997, 8 pages.
Fan, X. et al., "Modeling Transient Pupillary Light Reflex Induced by a Short Light Flash", IEEE Transactions on Biomedical Engineering, vol. 58, No. 1, Jan. 2011, 7 pages.
U.S. Appl. No. 62/551,708, entitled "Focus Stacking for Retinal Imaging", filed Aug. 29, 2017.
U.S. Appl. No. 62/573,324, entitled "Flash Optimizing During Retinal Burst Imaging", filed Oct. 17, 2017.

* cited by examiner

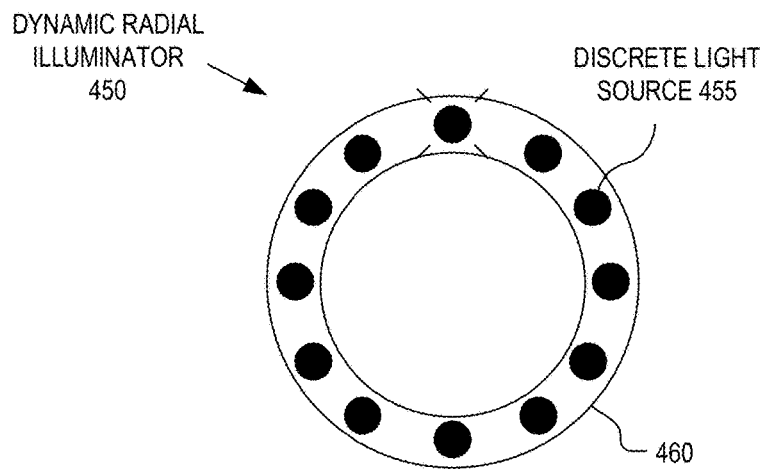
FIG. 4C
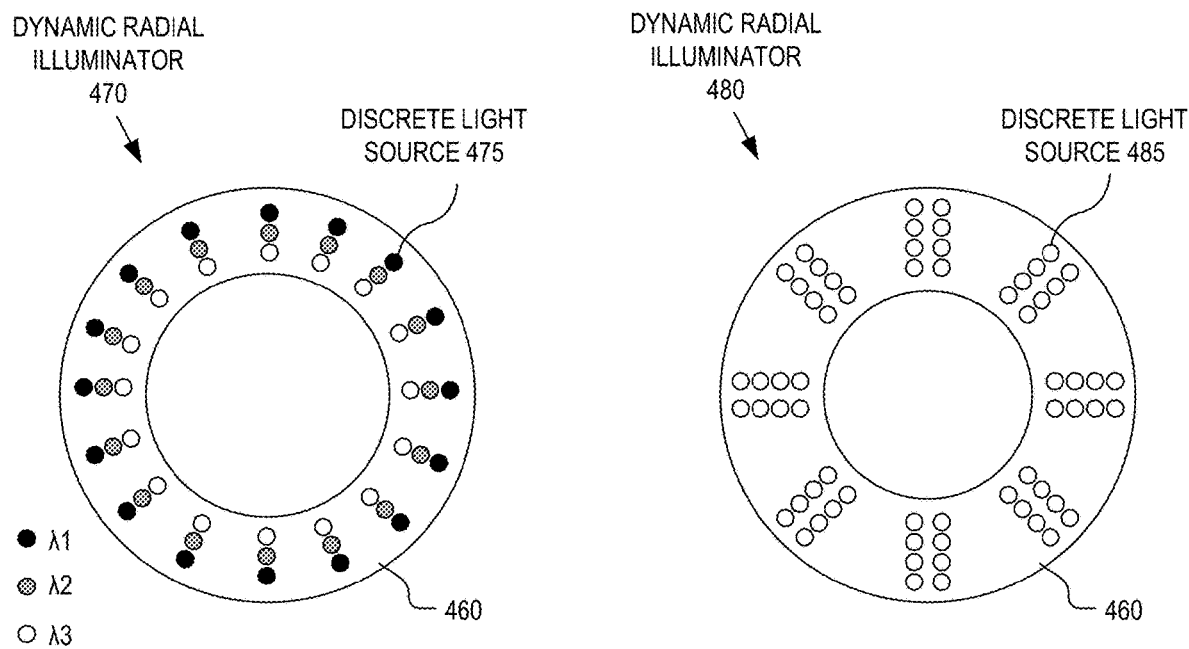
FIG. 4D  FIG. 4E

DYNAMIC ILLUMINATION DURING RETINAL BURST IMAGING

CROSS REFERENCE TO RELATED APPLICATION

This application claims the benefit of U.S. Provisional Application No. 62/545,234, filed Aug. 14, 2017, which is hereby incorporated by reference in its entirety.

TECHNICAL FIELD

This disclosure relates generally to imaging technologies, and in particular, relates to retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity while often creating optical aberrations or image artifacts, such as lens flare. Lens flare is a phenomenon where light scatters off of interior components of a lens system due to internal reflections, refractive index changes at various internal boundaries, imperfections, or otherwise. This scattered light shows up in the retinal image as lens flare, which is deleterious to the image quality. The brighter the illumination, the more pronounced the lens flare, which undermines the goal of improving image fidelity. Other image artifacts may arise due to corneal reflections or iris reflections from misalignment with the pupil.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 4A-E illustrate demonstrative dynamic radial illuminators, in accordance with embodiments of the disclosure.

DETAILED DESCRIPTION

Embodiments of a system, apparatus, and method of operation for retinal burst imaging using dynamic illumination to reduce illumination artifacts are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

High fidelity retinal images are important for screening, diagnosing, and monitoring many retinal diseases. To this end, reducing or eliminating instances of image artifacts (e.g., deleterious corneal reflections, etc.) that occlude, or otherwise malign portions of the retinal image is desirable. Embodiments described herein combine multiple image frames of a retina illuminated with different illumination patterns to reduce the incidence of image artifacts in a composite retinal image.

Figure 1A:
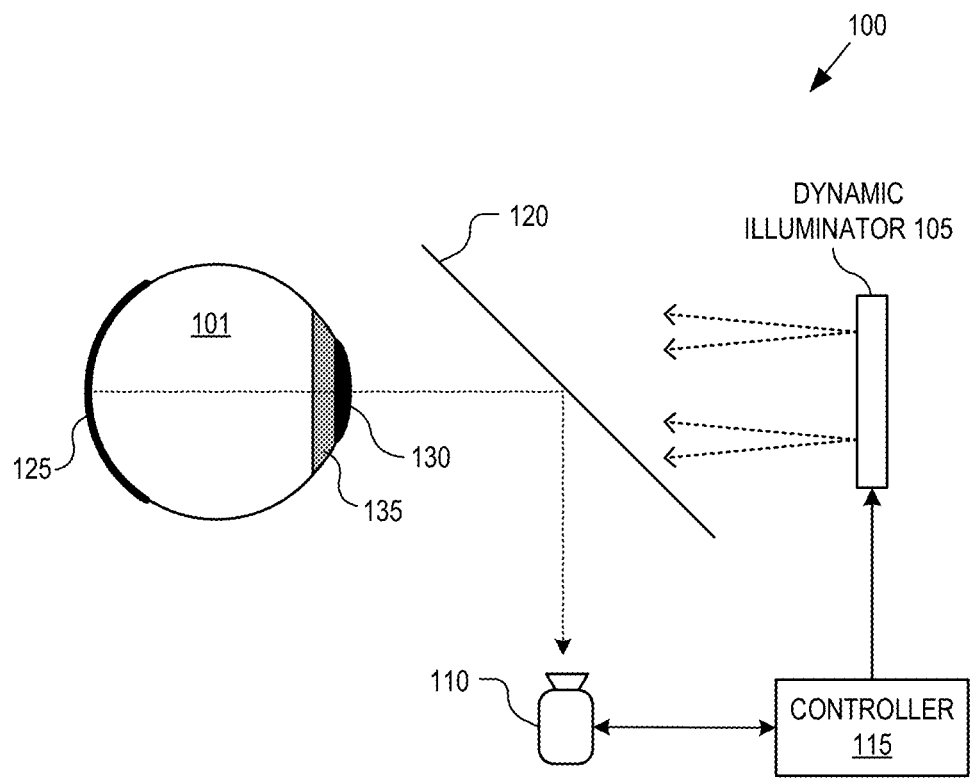
FIG. 1A illustrates a retinal burst imaging system using a dynamic illuminator, in accordance with an embodiment of the disclosure.

FIG. 1A illustrates a retinal burst imaging system 100, in accordance with an embodiment of the disclosure. The illustrated embodiment of imaging system 100 includes a dynamic illuminator 105, a retinal camera 110, a controller 115, and an optical relay system 120 capable of capturing burst image frames of a retina 125.

Optical relay system 120 serves to direct (e.g., pass) light from dynamic illuminator 105 through pupil 130 to illuminate retina 125 while directing (e.g., reflecting) imaging light of retina 125 to retinal camera 110. In the illustrated embodiment optical relay system 120 is a beam splitter. However, it should be appreciated that optical relay system 120 may be implemented with a number and variety of optical elements (e.g., lenses, reflective surfaces, etc.), such as the optical relay system illustrated in FIG. 5.

Controller 115 is coupled to retinal camera 110 and dynamic illuminator 105 to choreograph their operation. Controller 115 may include software/firmware logic executing on a microcontroller, hardware logic (e.g., application specific integrated circuit, field programmable gate array, etc.), or a combination of software and hardware logic. Although FIG. 1A illustrates controller 115 as a distinct functional element, the logical functions performed by controller 115 may be decentralized across a number hardware elements. For example, some of the image processing functions described below may be integrated into retinal camera 110 as an integrated signal processor (ISP), or performed on a discrete microprocessor external to retinal camera 110. Furthermore, controller 115 may include integrated or attached memory for buffering/storing image frames and composite retinal images. Controller 115 may further include input/output (I/O ports), communication systems, user interfaces, or otherwise.

Retinal camera 110 may be implemented using a variety of imaging technologies, such as complementary metal-oxide-semiconductor (CMOS) image sensors, charged-coupled device (CCD) image sensors, or otherwise. In one embodiment, retinal camera 110 includes an onboard memory buffer and ISP, as discussed in connection with FIG. 6.

During operation, controller 115 operates dynamic illuminator 105 and retinal camera 110 to capture a burst of image frames of retina 125 during a single imaging window through pupil 130. Dynamic illuminator 105 is dynamic in that its illumination pattern is not static; but rather, may be changed between image frames (e.g., changed responsive to controller 115). In some embodiments, a single imaging window is an amount of time available to image retina 125 through pupil 130 prior to iris 135 substantially closing due to the illumination patterns output from dynamic illuminator 105. In various embodiments, the single imaging window corresponds to a duration of less than 500 msec. In other embodiments, the single imaging window corresponds to a duration of less than 200 msec. In one embodiment, the single imaging window is approximately 100 ms. In yet other embodiments, the single imaging window can be longer, lasting up to 5 seconds. Between capturing one or more of the image frames within an imaging burst or single imaging window, controller 115 reconfigures dynamic illuminator 105 to output different illumination patterns. In one embodiment, the different illumination patterns illuminate retina 125 from different angular positions about the field of view (FOV) of retina 125. Of course, the different illumination patterns may include other reconfigurations of dynamic illuminator 105, as discussed below. These different illumination patterns cause image artifacts to appear in different regions of the image frames. Accordingly, by acquiring multiple different image frames illuminated with different illumination patterns, a high quality composite retinal image can be generated where few or no regions of the composite retinal image are obstructed by an image artifact. Image artifacts may arise from reflections off the cornea of eye 101, reflections off of iris 135 due to misalignment of dynamic illuminator 105 with pupil 130, lens flare, or otherwise.

Figure 1B:
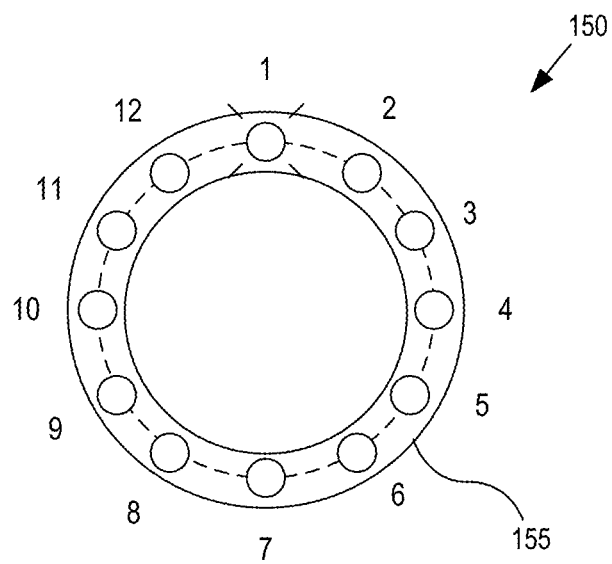
FIG. 1B illustrates a frontal view of a dynamic illuminator, in accordance with an embodiment of the disclosure.

FIG. 1B illustrates a frontal view of an example dynamic radial illuminator 150, in accordance with an embodiment of the disclosure. Dynamic radial illuminator 150 represents a demonstrative implementation of dynamic illuminator 105 where illumination locations are radially disposed about an annular region 155. Accordingly, dynamic radial illuminator 150 represents a radial implementation; however, it should be appreciated that dynamic illuminator 105 may be implemented with other configurations (radial or otherwise) capable of achieving a dynamically changing illumination.

As illustrated in FIG. 1B, dynamic radial illuminator 150 includes twelve discrete illumination locations 1 through 12 each having a different angular position about the FOV of retina 125. During operation, retinal camera 110 and dynamic radial illuminator 150 may be operated by controller 115 to acquire one or more image frames while retina 125 is separately illuminated from each illumination location 1 through 12. In other embodiments, groups of illumination locations 1 through 12 are enabled per image frame. These grouped illumination locations may be contiguous locations or non-contiguous illumination locations about annular region 155.

Figure 2A:
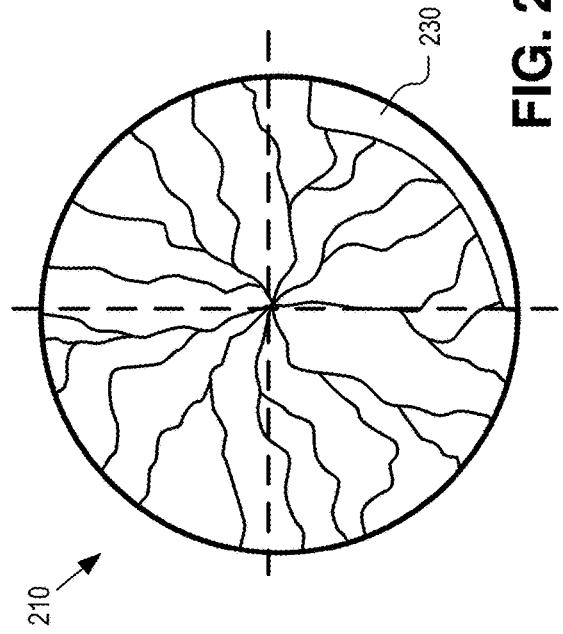
FIGS. 2A-D illustrate image frames of a retina captured with different illumination patterns, in accordance with an embodiment of the disclosure.
Figure 2B:
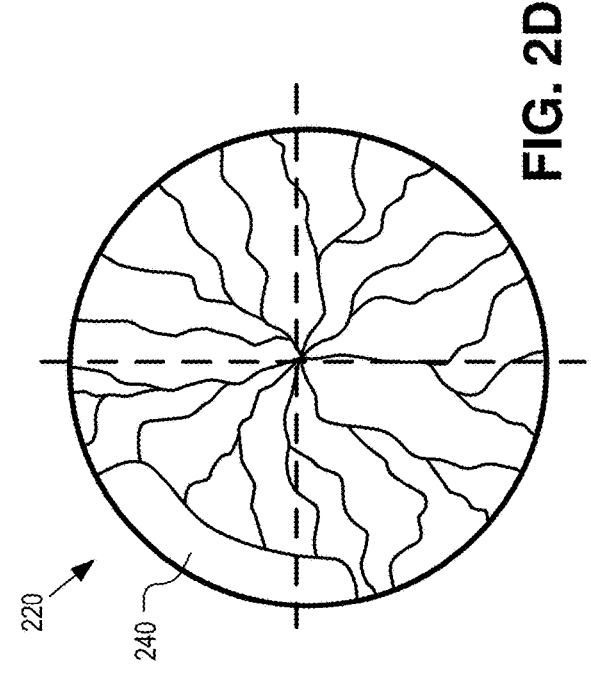
Figure 2C:
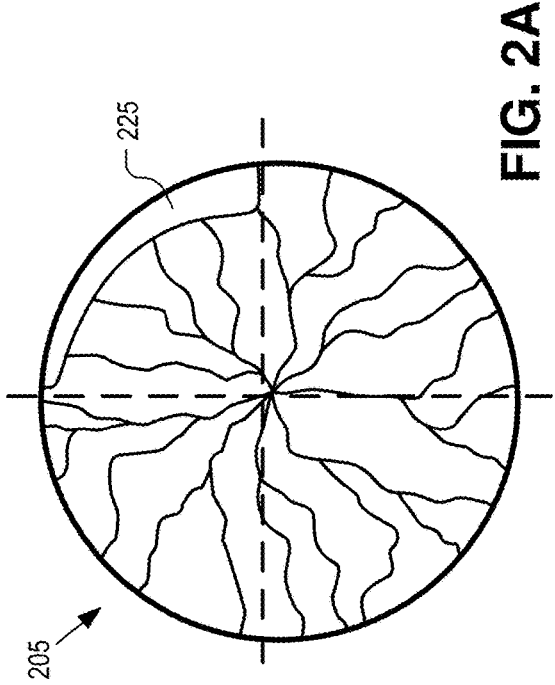
Figure 2D:
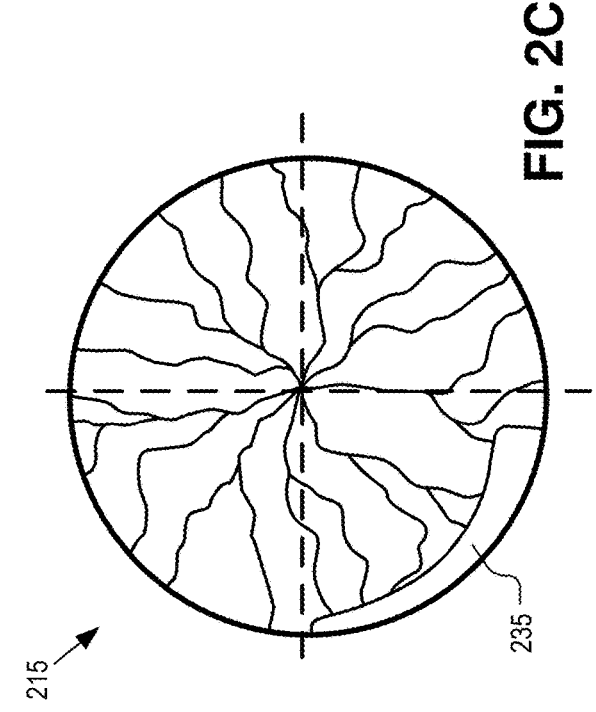

FIGS. 2A-D illustrate four image frames of retina 125 captured with four different illumination patterns, in accordance with an embodiment of the disclosure. For example, FIG. 2A illustrates an example image frame 205 of retina 125 having an image artifact 225 in the upper right quadrant of the image. Image artifact 225 may be a corneal reflection, a reflection or obstruction due to iris 135, lens flare, or otherwise. As such, the upper right quadrant of image frame 205 may be deemed a defect region with an unacceptable image artifact while the other three quadrants of image frame 205, which do not include a significant image artifact, may be deemed usable regions for the composite retinal image. Correspondingly, the lower right quadrant of image frame 210, which includes image artifact 230, may be deemed to be a defect region; the lower left quadrant of image frame 215, which includes image artifact 235, may be deemed to be a defect region; and the lower left and upper left quadrants of image frame 220, which include portions of image artifact 240, may be deemed to be a defect regions. It should be appreciated that image artifacts can appear anywhere in the image frames, including the central region, and not just along the perimeter as illustrated in FIGS. 2A-2D. Although FIGS. 2A-D illustrate the image frames divided into quadrants, the image frames may be segmented in any number of regions having a variety of different shapes. In one embodiment, the defect regions may be limited to the size and shape of the image artifacts themselves. The regions without significant image artifacts may be deemed usable regions that are acceptable for combination into the composite retinal image. By aligning and cropping the retinal images 205, 210, 215, and 220, and disregarding or de-emphasizing the defect regions while combining the usable regions, a single, high quality, defect free, composite retinal image that covers the full region of interest or FOV of retina 125 can be acquired.

As mentioned above, image artifacts 225-240 may occur for a variety of reasons. In the case of corneal reflections, image artifacts tend to appear on the opposite side of the image frame from the illumination location. Accordingly, if image artifact 230 is caused by a corneal reflection, then it is possible retina 125 was being illuminated from illumination locations 10-12 and 1. In this scenario, reimaging retina 125 while illuminated from other locations may achieve a lower right quadrant image that is usable or substantially defect free.

In the case of a reflection or obstruction due to iris 135, dynamic illuminator 105 may have been misaligned with pupil 130 when illuminated from illumination locations 1-4. Such misalignment may result in deleterious reflections in the upper right quadrant of image frame 205, as illustrated. To correct this image defect, retina 125 may be reimaged using illumination locations 7-10 opposite the defect region in the upper right quadrant of image frame 205.

Figure 3:
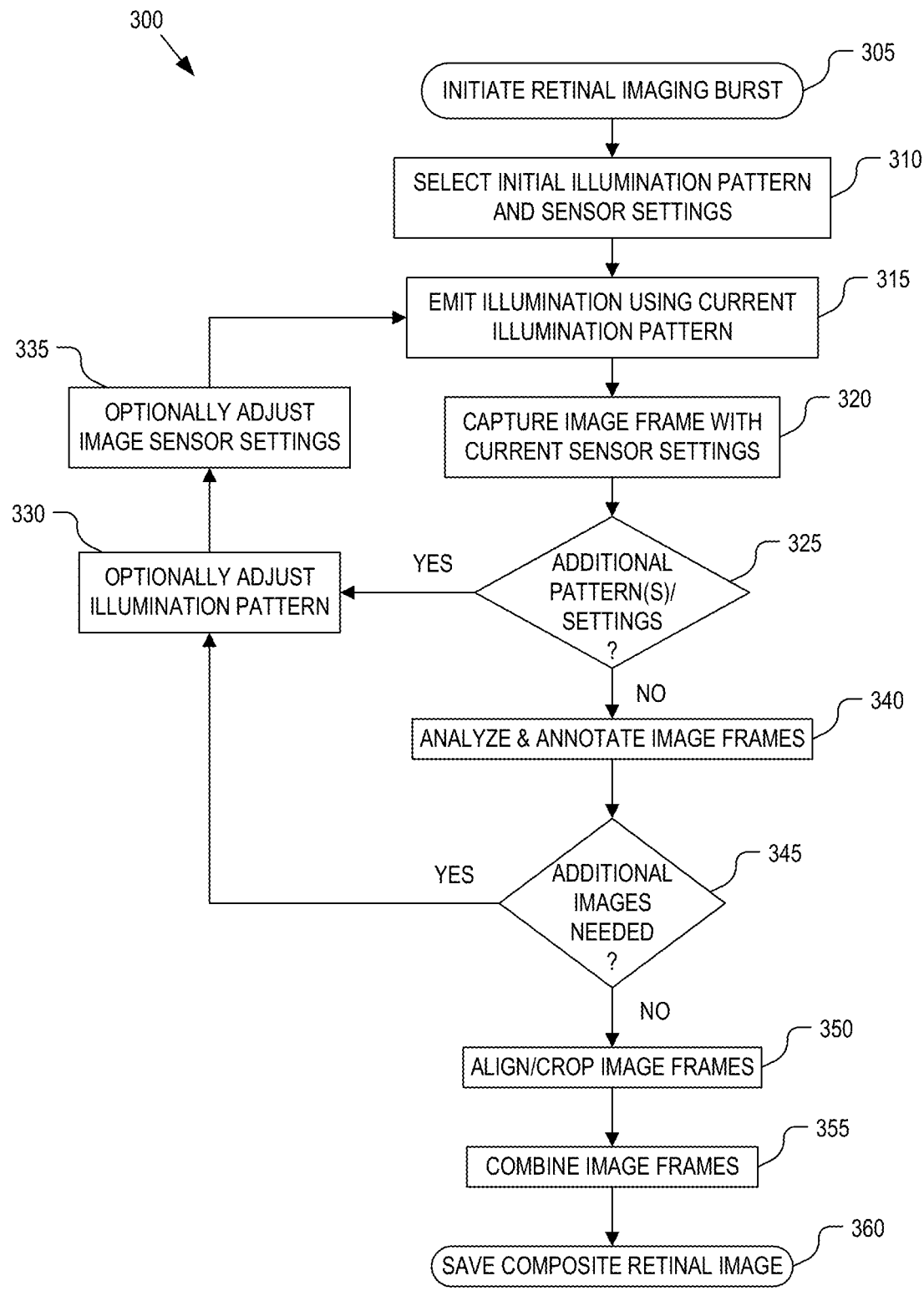
FIG. 3 is a flow chart illustrating a process of operation of a retinal burst imaging system using a dynamic illuminator, in accordance with an embodiment of the disclosure.

FIG. 3 is a flow chart illustrating a process 300 of operation of retinal imaging system 100, in accordance with an embodiment of the disclosure. The order in which some or all of the process blocks appear in process 300 should not be deemed limiting. Rather, one of ordinary skill in the art having the benefit of the present disclosure will understand that some of the process blocks may be executed in a variety of orders not illustrated, or even in parallel.

In a process block 305, a retinal imaging burst is initiated by controller 115. In one embodiment, initiation is triggered in response to user input (e.g., button press). In yet another embodiment, initiation may be automatically triggered based upon a gaze tracking system (e.g., iris/pupil tracking camera) that triggers a retinal imaging burst when the gaze of eye 101 is sufficiently aligned with optical relay system 120.

In a process block 310, an initial illumination pattern for dynamic illuminator 105 and/or initial sensor settings for retinal camera 110 are selected. These initial settings may be default settings or dynamically selected by controller 115 based upon real-time feedback from retinal camera 110. For example, environmental conditions or characteristics of eye 101 may alter selection of the initial illumination pattern and sensor settings.

In a process block 315, dynamic illuminator 105 is enabled to emit an illumination pattern, as previously selected, which provides lighting for imaging by retinal camera 110. Once dynamic illuminator 105 is enabled, the single imaging window along with the iterative dynamic illumination and image capturing begins. In a process block 320, retinal camera 110 captures an image frame of retina 125 with the currently selected sensor settings. If additional image frames are to be acquired (decision block 325), then process 300 continues to process block 330, where the illumination pattern may be adjusted, and process block 335, where the image sensor settings may be adjusted, prior to re-illuminating and capturing the next image frame at process blocks 315 and 320.

The number of image frames captured during a single imaging window may be four or greater image frames. In various embodiments, 16 frames, 24 frames, 48 frames, or even more than 48 frames may be captured during a single imaging window. The illumination pattern and/or the camera settings may be adjusted between each image frame or between groups of image frames such that multiple image frames are acquired with the same illumination pattern and/or the same image sensor settings. Adjusting the illumination pattern in process block 330 may include one or more of changing illumination positions about annular region 155 to illuminate retina 125 from different angular or radial positions, changing a brightness of the illumination, changing an illumination wavelength (e.g., changing between red, green, blue, infrared, white light, or other wavelengths), changing an illumination duration between image frames, or other illuminator settings. Adjusting the image sensor settings in process block 335 may include one or more of changing a gain setting, an exposure duration, an aperture setting, or other sensor settings.

Once it is determined that all initial image frames have been acquired (decision block 325), process 300 continues to a process block 340. In process block 340, the captured image frames are optionally analyzed to identify defect regions deemed to include an unacceptable image artifact (or usable regions deemed to be acceptable). These regions (either defect regions or usable regions) are optionally annotated as such.

In decision block 345, it is determined whether additional image frames should be acquired before expiration of the single imaging window. In one embodiment, this determination is based upon the analysis and annotations in process block 340. Accordingly, in one embodiment, controller 115 determines whether any region of interest of retina 125 has been imaged with insufficient quality. If any region of interest has been imaged with insufficient quality, process 300 returns to process blocks 330 to reconfigure dynamic illuminator 105 with one or more additional illumination patterns that reduce image artifacts in the region of interest imaged with insufficient quality and one or more additional image frames acquired (process block 320). In one embodiment, these additional image frames are also acquired prior to the single imaging window closing.

Once all regions of interest have been imaged with sufficient quality, and therefore deemed useable (or the single imaging window expires), process 300 exits the iteration loops. The image frames are then aligned to each other and cropped to a common retinal FOV (process block 350), combined (process block 355), and saved as a composite retinal image (process block 360). In various embodiments, the image frames may be combined (e.g., stacked, stitched, etc.) in a number of different manners. In one embodiment, a weighting is applied to the defect or useable regions of the image frames to disregard, or otherwise de-emphasize, the defect regions thereby giving greater weight to the useable regions. In another embodiment, the image frames are averaged together with the assumption that good images of any particular pixel will outweigh defect images of that pixel. In one embodiment, only useable regions are combined.

Image stacking techniques for combining a burst of image frames may include the preliminary step of a phase correlation on the image frames to determine the translational offset. Once determined, the image frames are shifted by that amount in the opposite direction to correct the offset, and the edges are zero padded (process block 350). The stack of aligned images may then be composited into a single image (process block 355) with more favorable signal-to-noise ratio (SNR) with anyone one of the below three example methods (or other methods).

Averaging: All non-zero padded pixels with the same x/y coordinates are averaged across all images in the stack. In one embodiment, an incremental averaging algorithm is used so that it is not necessary to maintain an entire stack in memory at the same time.

Sigma-clipped Averaging: This technique is similar to averaging, except that the standard deviation of each pixel stack (all pixels with the same image space coordinates) is computed and outliers are rejected. The cutoff point for outliers is the average value +/− some multiplicative factor of the standard deviation, or some multiplicative factor of a fixed standard deviation value, which corresponds to the predetermined standard deviation of noise in a given camera setup. For example, values above 2.1 may be used as the multiplicative factor. This is an incremental algorithm, but two or more passes are expected—one pass to compute an average and standard deviation image from the stack, and another pass to compute the incremental average that clips outliers.

The performance of sigma-clipped averaging may be improved with nonlinear logic in determining cutoff points. For example, if there are only two cases: with lens flare and without lens flare, then the brightness distribution across the stack for each pixel should be bimodal. The lower mode corresponds to the true values, and the higher mode corresponds to the lens flare. In this case, one might want to clip above the midpoint between the modes in order to reject the majority of the samples containing lens flare. Choice of a good policy is dependent on the characteristics of noise in a real system.

Median: The median value of all non-zero-padded pixels with the same x/y coordinates is used. This is NOT an incremental algorithm and uses all image frames at compositing time.

FIGS. 4A-E illustrate demonstrative dynamic radial illuminators, in accordance with embodiments of the disclosure.

The dynamic radial illuminators illustrated in FIGS. 4A-E represent possible implementations of dynamic illuminator 105 illustrated in FIG. 1A.

Figure 4A:
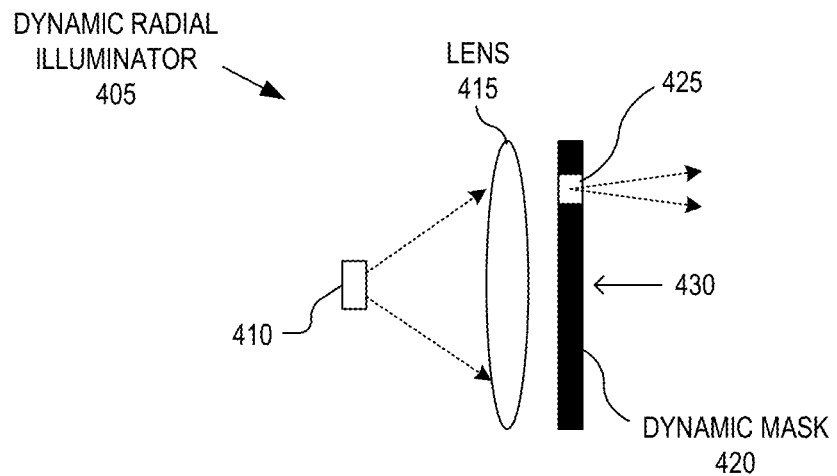

FIG. 4A illustrates a dynamic radial illuminator that includes a light source 410, a lens 415, and a dynamic mask 420. Light source 410 may be implemented as a point source that is collimated (or merely reduces light divergence) by lens 415. In one embodiment, light source 410 is a light emitting diode (LED). Dynamic mask 420 includes a repositionable hole 425 to pass illumination light when illuminated from its backside by light source 410. The position of hole 425 may be moved radially from a center 430 or angularly about center 430. In one embodiment, dynamic mask 420 is a rotatable opaque mask with one or more holes 425 that are repositioned by rotating mask 420. In yet other embodiments, dynamic mask 420 may be a spatial light modulator (SLM), such as an electro-chromatic dimmable window or liquid crystal display (LCD) with polarizer, capable of repositioning hole 425 under the influence of controller 115. In other embodiments, dynamic mask 420 may be frontside illuminated and repositionable hole 425 replaced with a repositionable reflective element.

Figure 4B:
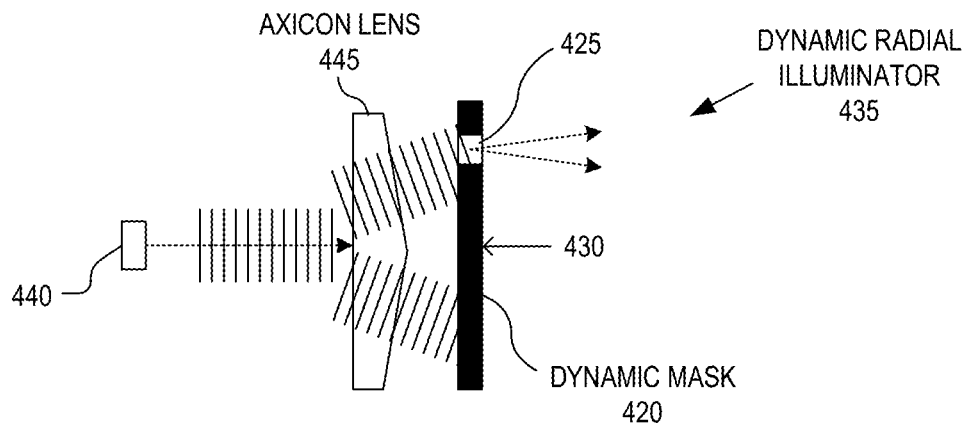

FIG. 4B illustrates a dynamic radial illuminator 435 that includes a light source 440, an axicon lens 445, and dynamic mask 420. Dynamic radial illuminator 435 is similar to dynamic radial illuminator 405 except that light source 440 is a laser source that is transformed into a ring of light for illuminating the backside of dynamic mask 420 by axicon lens 445.

FIG. 4C illustrates a dynamic radial illuminator 450 that includes a plurality of discrete light source 455 disposed around an annular region 460 (e.g., annular substrate). The annular region 460 is positioned to encircle a FOV of retina 125 and the different illumination patterns are emitted from annular region 460. The FOV may be physically encircled by having the user look through the center of annular region 460 or optically encircled using an optical relay system to image the annular region 460 about the FOV of retina 125. This is likewise applicable to the other dynamic illuminators described herein.

The discrete light sources 455 are coupled to controller 115 for individual control and illumination. An individual one of discrete light sources 455 may be illuminated for point source illumination. Alternatively, multiple selected ones of discrete light sources 455 may be simultaneously illuminated. In one embodiment, discrete light sources 455 are LEDs. The LEDs may be all the same color, multiple different colors, each monochromatic or each broad spectrum. Furthermore, the LEDs may emit light in the visible band and/or the infrared (IR) band.

FIG. 4D illustrates a dynamic radial illuminator 470 where the discrete light sources 475 are multicolor and disposed around annular region 460 with both varying angular positions and radial positions. Although FIG. 4D illustrates the discrete light sources 475 having three different colors or wavelengths, in other embodiments, more or less colors/wavelengths in the visible or infrared spectrum may be used. Similarly, other embodiments may include more or less than three radial positions for discrete light sources 475. In yet other embodiments, one or more of discrete light sources 475 may be overlaid with polarizers (either linear or circular). For example, a portion of the discrete light sources 475 may include horizontal or left-circular polarizing films while others may include vertical or right-circular polarizing films. In one embodiment, microlenses may be disposed over discrete light sources 475.

FIG. 4E illustrates another example dynamic radial illuminator 480 where the discrete light sources 485 are disposed around annular region 460 with both varying angular positions and radial positions. Dynamic radial illuminator 480 has a similar configuration as illuminator 470. In various embodiments, discrete light source 485 may be white LEDs, IR LEDs, or a combination of white and IR LEDs. Furthermore, discrete light sources 485 may be covered with an illumination baffle that is opaque and constrains the size and shape of the illumination apertures of each discrete light source 485. In one embodiment, the illumination baffle may also constrain the divergence of the individual light cones emitted from each discrete light source 485. The light baffle may also serve to ensure segmentation and isolation of the light cones emitted from each discrete light source 485 and reduce or prevent cross-contamination between discrete light sources 485. Of course, the illumination baffle may be included over any of the dynamic radial illuminators discussed above.

Figure 5:
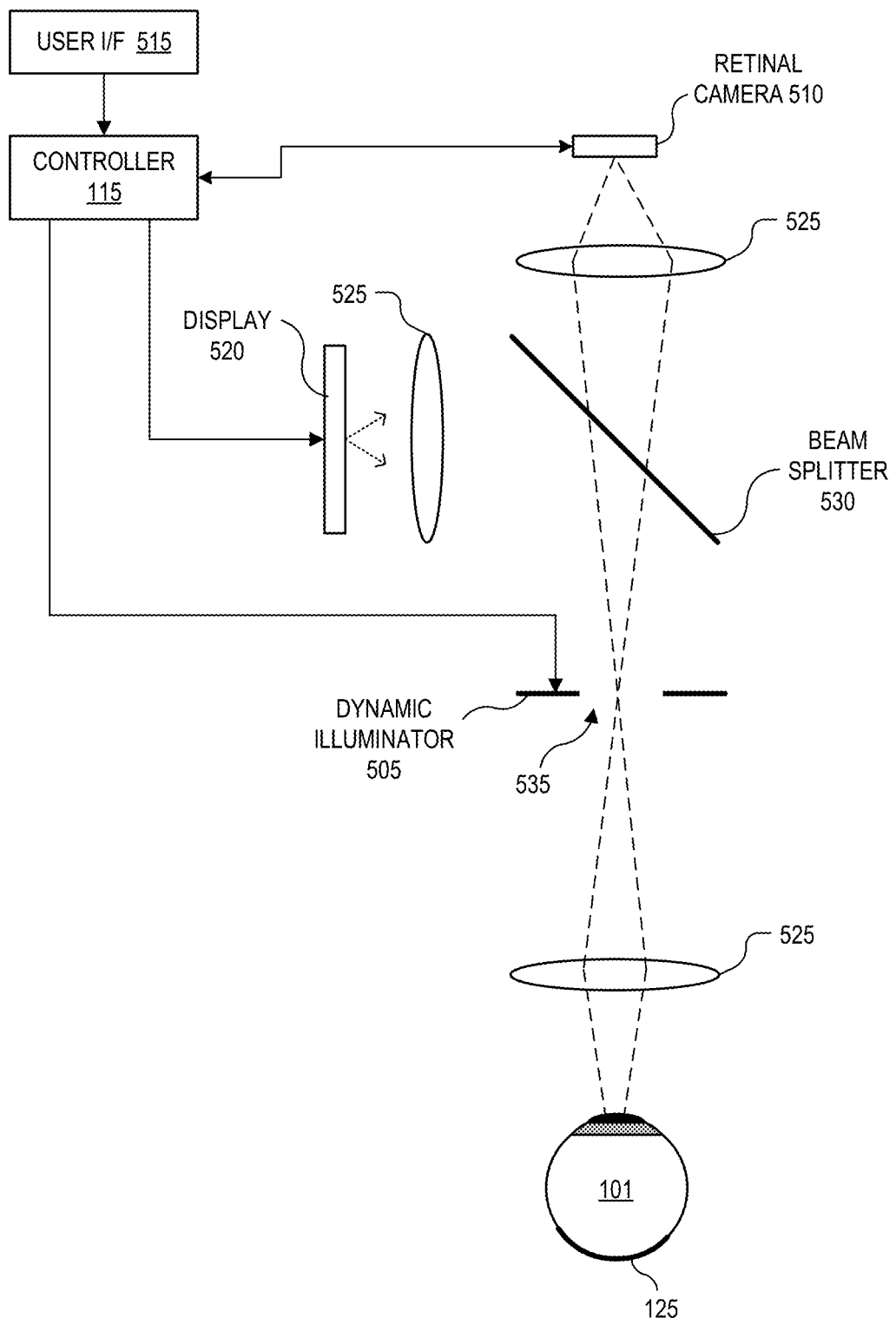
FIG. 5 is a diagram illustrating an demonstrative retinal imaging system using a dynamic illuminator, in accordance with an embodiment of the disclosure.

FIG. 5 is a diagram illustrating a demonstrative retinal imaging system 500 using a dynamic illuminator, in accordance with an embodiment of the disclosure. Retinal imaging system 500 is one possible implementation of retinal imaging system 100. The illustrated embodiment of retinal imaging system 500 includes a dynamic radial illuminator 505, a retinal camera 510, controller 115, a user interface 515, a display 520, and an optical relay system that includes lenses 525 and a beam splitter 530. System 500 operates in the same manner as described in connection with system 100 and process 300.

A central section 535 of dynamic illuminator 505 is physically positioned in the optical path about the FOV of retinal 125. In some embodiments, the annular region of dynamic illuminator 505 operates as a stop to block many off-axis deleterious reflections before reaching retinal camera 510. The retinal images are passed through central section 535 to retinal camera 510. In addition to reducing image artifacts due to deleterious reflections from the cornea, the use of multiple illumination locations about the annular region of dynamic illuminator 505 also serves to increase the eyebox of system 500. The eyebox is the region in space where eye 101 can be located and imaged. In some embodiments, all or some of discrete light sources (e.g., point light source) of dynamic illuminator 505 are disposed outside (e.g., peripheral to) a perimeter of the imaging path extending from retina 125 to retinal camera 510. In other embodiments, one or more of the discrete light sources of dynamic illuminator 505 are disposed inside the perimeter of the imaging path to retinal camera 510.

In one embodiment, central section 535 is coated with one or more optical films (e.g., dichroic coatings) to substantially pass light with wavelengths below 900 nm while substantially reflecting light above 900 nm to facilitate the use of infrared (IR) gaze tracking. In one embodiment, an iris camera (not illustrated) is laterally disposed to aid IR gaze tracking. An iris camera may operate to track gross movements of eye 101, such as blinking and gaze tracking, by tracking or imaging the iris and/or the pupil of eye 101.

Beam splitter 530 is positioned to pass a portion of the light of retinal images to retinal camera 510 while reflecting display light output from display 520 to eye 101. The display light may include a fixation target or other visual stimuli to aid retinal alignment during imaging. In some embodiments, beam splitter 530 is more transmissive than reflective. In one embodiment, beam splitter 530 is approximately 90% transmissive and 10% reflective. Other reflectance/transmittance ratios may be implemented. Lenses 525 are provided throughout system 500 to provide image and light focusing in the optical paths. User interface 515 provides a mechanism to commence burst image capture. In one embodiment, user interface 515 is a button.

Figure 6:
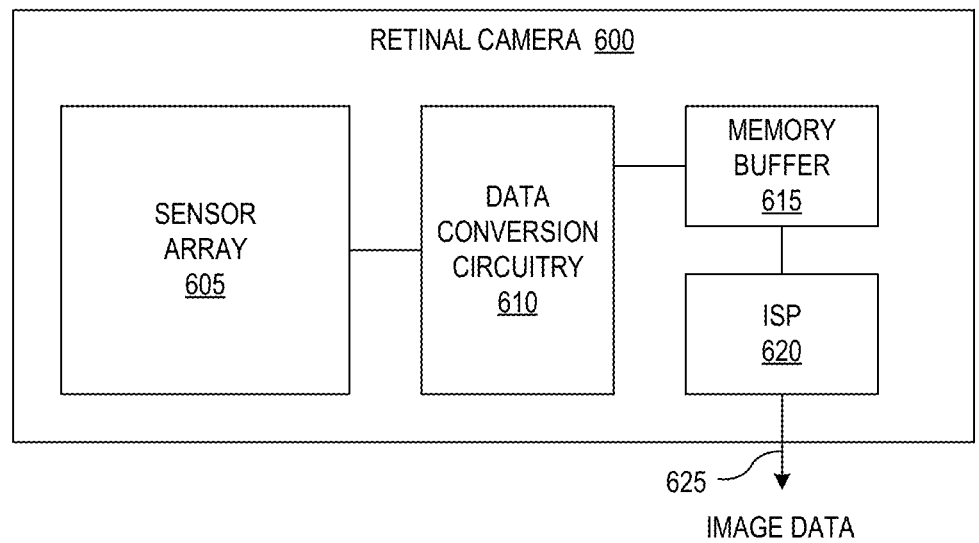
FIG. 6 is a functional block diagram of a retinal camera including an integrated image signal processor, in accordance with an embodiment of the disclosure.

FIG. 6 is a functional block diagram of a retinal camera 600 including an integrated image signal processor, in accordance with an embodiment of the disclosure. Retinal camera 600 is one possible implementation of retinal camera 110 (or 510). The illustrated embodiment of retinal camera 600 includes a two-dimensional sensor array 605, data conversion circuitry 610, a memory buffer 615, an integrated image signal processor (ISP) 620, and an output port 625.

During operation, two-dimensional image data (e.g., retinal images) is acquired by sensor array 605 and converted from the analog domain to the digital domain by data conversion circuitry 610. The image data may be acquired at a high frame rate (e.g., 24, 48, 60, 240, 1000 frames per second) and stored into memory buffer 615. ISP 620 operates on the buffered retinal image frames to identify useable or defect regions, annotate the regions of interest in the image frames, and/or combine the useable regions into high quality, composite retinal images. Accordingly, in one embodiment, some of the image processing tasks described above may be off-boarded to ISP 620 from controller 115. ISP 620 may be considered a logical subcomponent of controller 115.

Figure 7:
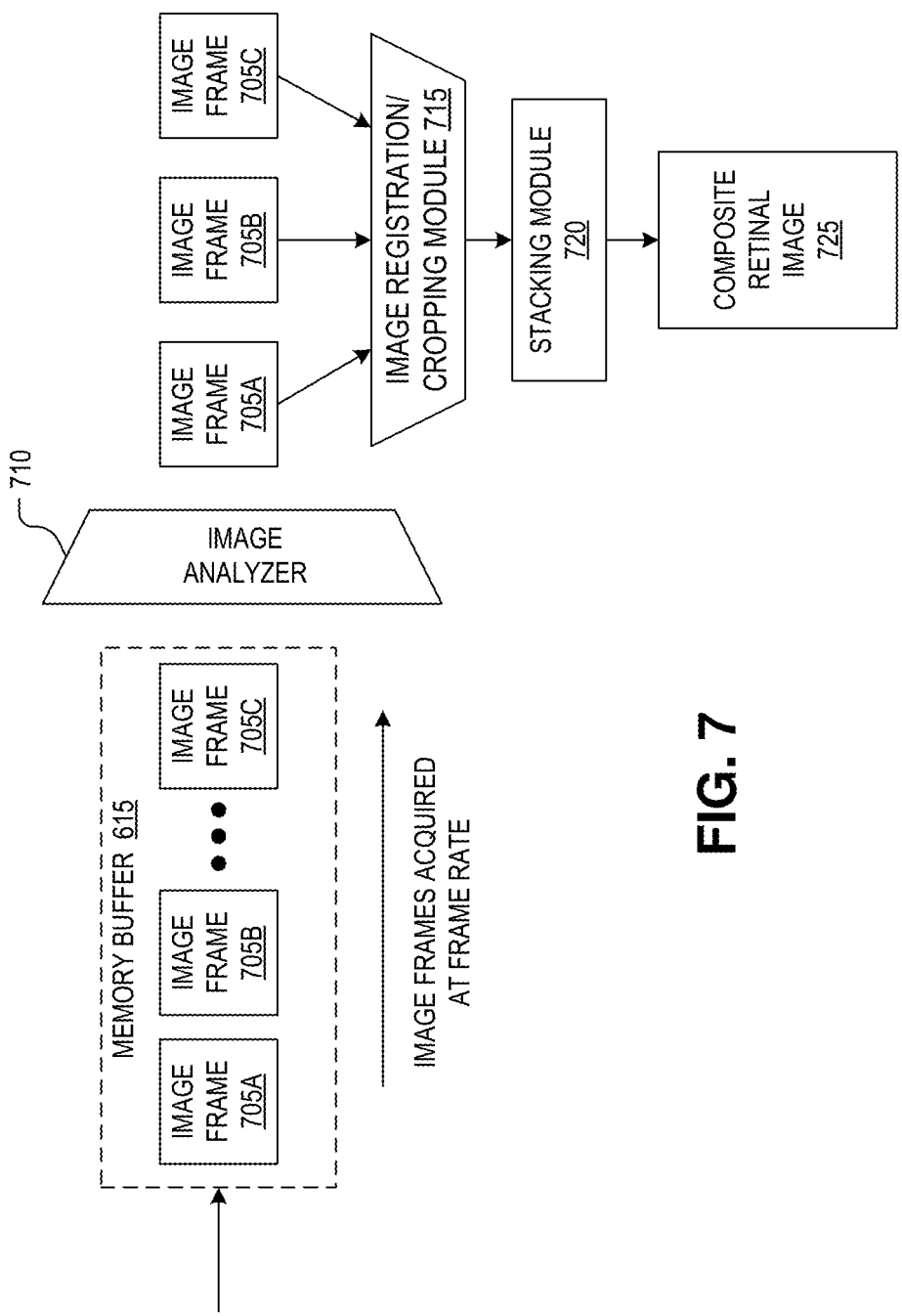
FIG. 7 is a block flow diagram illustrating image processing by a retinal camera including an integrated image signal processor, in accordance with an embodiment of the disclosure.

FIG. 7 is a block flow diagram illustrating image processing by retinal camera 600 that leverages the benefits of having the integrated ISP 620 to acquire high quality composite retinal images, in accordance with an embodiment of the disclosure. As illustrated, image frames 705A-C of retina 125 are acquired by sensor array 605 at a high frame rate, converted into the digital domain by data conversion circuitry 610, and buffered into memory buffer 615. An image analyzer 710 is executed by ISP 620 to analyze the buffered retinal images 705 (a sort of preprocessing) to determine which portions of images frames 805 are of sufficient quality and which are of insufficient quality due to unacceptable image artifacts. For example, image analyzer 710 may analyze image frames 705 for blurred portions, portions that do not have sufficient contrast to be useful, are washed out, and/or include unacceptable corneal or iris reflections, or lens flare. Image portions that are deemed unacceptable are flagged unacceptable (e.g., marked or annotated) while image portions that are deemed acceptable are flagged as such. The image frames are then registered to each other (e.g., pixel-to-pixel alignment), cropped to a common FOV by image registration/cropping module 715, and then combined by stacking module 720 into a single composite retinal image 725. Stacking module 720 may combine images to generate high dynamic range images. In other embodiments, image frames 705 are simply combined without analysis and/or annotation of the individual image frames.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method of imaging a retina, comprising:
    configuring a dynamic illuminator to illuminate the retina with an illumination pattern;
    capturing a two-dimensional (2D) image frame of the retina with a 2D sensor array while the retina is illuminated with the illumination pattern, wherein the illumination pattern is unchanged while acquiring the 2D image frame;
    iterating the configuring and the capturing to sequentially reconfigure the dynamic illuminator to illuminate the retina with a plurality of different illumination patterns and capture a plurality of image frames, including the 2D image frame, wherein each of the image frames is a 2D image that is illuminated with one of the different illumination patterns; and
    combining at least a subset of the image frames into a composite retinal image.

2. The method of claim 1, wherein capturing the plurality of image frames includes capturing a burst of image frames during a single imaging window through a pupil, wherein the single imaging window is configured with a duration that finishes the burst prior to an iris of an eye substantially closing due to the different illumination patterns.

3. The method of claim 2, wherein the single imaging window comprises a duration of less than 500 milliseconds.

4. The method of claim 2, wherein the plurality of image frames comprises greater than or equal to 16 frames.

5. The method of claim 2, further comprising:
    analyzing each of the image frames to identify defect regions deemed to include an unacceptable image artifact or usable regions deemed acceptable; and
    annotating the image frames to indicate the defect regions or the usable regions,
    wherein combining the image frames comprises combining the usable regions.

6. The method of claim 5, wherein the unacceptable image artifact comprises a corneal reflection from one or more of the different illumination patterns.

7. The method of claim 5, wherein combining the image frames comprises applying a weighting that disregards or de-emphasizes the defect regions.

8. The method of claim 5, further comprising:
    determining whether any region of interest of the retina is imaged with insufficient quality based upon the analyzing; and in response to determining a region of interest of the retina is imaged with insufficient quality, configuring the dynamic illuminator to illuminate the retina with an additional illumination pattern that reduces image artifacts in the region of interest imaged with insufficient quality; and acquiring one or more additional image frames while illuminating the retina with the additional illumination pattern prior to the single imaging window closing.

9. The method of claim 1, wherein combining the image frames comprises averaging the image frames.

10. The method of claim 1 further comprising:
aligning the image frames prior to combining the image frames.

11. The method of claim 1, further comprising:
changing image sensor settings between one or more iterations of capturing the image frames.

12. The method of claim 1, wherein sequentially reconfiguring the dynamic illuminator to illuminate the retina with the plurality of different illumination patterns includes one or more of:

changing illumination positions about an annular region of the dynamic illuminator to illuminate the retina from different angular or radial positions between one or more of the different illumination patterns;

changing a brightness between one or more of the different illumination patterns;

changing an illumination wavelength between one or more of the different illumination patterns; or changing an illumination duration between one or more of the different illumination patterns.

13. A retinal imaging system, comprising:
a retinal camera having a two-dimensional (2D) sensor array;
a dynamic illuminator;
an optical relay system to optically relay light between the retinal camera, the dynamic illuminator and a retina; and
a controller coupled to control the retinal camera and the dynamic illuminator, the controller including logic that when executed causes the retinal imaging system to perform operations including:
configuring the dynamic illuminator to illuminate the retina with an illumination pattern;
capturing a 2D image frame of the retina while illuminated with the illumination pattern, wherein the illumination pattern is unchanged while acquiring the 2D image frame;
iterating the configuring and the capturing to sequentially reconfigure the dynamic illuminator to illuminate the retina with a plurality of different illumination patterns and capture a plurality of image frames, including the 2D image frame, wherein each of the image frames is a 2D image that is illuminated with one of the different illumination patterns; and
combining at least a subset of the image frames into a composite retinal image.

14. The retinal imaging system of claim 13, wherein the dynamic illuminator comprises a dynamic radial illuminator having an annular region that encircles a field of view (FOV) of the retina and the different illumination patterns are emitted from the annular region.

15. The retinal imaging system of claim 14, wherein the dynamic radial illuminator comprises:

a dynamic mask coupled to generate the different illumination patterns about the annular region;
a light source to illuminate a backside of the dynamic mask; and
a lens disposed between the light source and the dynamic mask.

16. The retinal imaging system of claim 15, wherein the dynamic mask comprises one of:
a rotatable opaque mask having one or more holes to pass light from the light source, or
a spatial light modulator.

17. The retinal imaging system of claim 15, wherein the lens comprises an axicon lens and the light source comprises a laser source.

18. The retinal imaging system of claim 14, wherein the dynamic radial illuminator comprises a plurality of discrete light sources disposed around the annular region.

19. The retinal imaging system 18, wherein the discrete light sources comprise a plurality of different wavelength light emitting diodes.

20. The retinal imaging system of claim 18, wherein the discrete light sources are disposed around the annular region with different angular positions and different radial positions.

21. The retinal imaging system of claim 18, wherein one or more of the discrete light sources are overlaid by a polarizing film or a microlens.

22. The retinal imaging system of claim 13, wherein the plurality of image frames are captured as a burst of image frames during a single imaging window through a pupil prior to an iris substantially closing due to the different illumination patterns.

23. The retinal imaging system of claim 22, wherein the controller includes further logic that when executed causes the retinal imaging system to perform further operations including:
analyzing each of the image frames to identify defect regions deemed to include an unacceptable image artifact or usable regions deemed acceptable; and
annotating the image frames to indicate the defect regions or the usable regions,
wherein combining the image frames comprises combining the usable regions.

24. The retinal imaging system of claim 23, wherein combining the image frames comprises applying a weighting that disregards or de-emphasizes the defect regions.

25. The retinal imaging system of claim 13, wherein the controller includes further logic that when executed causes the retinal imaging system to perform further operations including:
changing settings of the retinal camera between one or more iterations of capturing the image frames, wherein the settings include one or more of an exposure time or a gain.

26. The retinal imaging system of claim 13, wherein the dynamic illuminator includes at least one point light source for generating one or more of the different illumination patterns disposed inside a perimeter of an imaging path of the retinal camera.

27. The retinal imaging system of claim 13, wherein the dynamic illuminator includes at least one point light source for generating one or more of the different illumination patterns disposed outside a perimeter of an imaging path of the retinal camera.

* * * * *